United States Patent
Horwitz

(12) 
(10) Patent No.: US 6,228,359 B1
(45) Date of Patent: May 8, 2001

(54) USE OF CYTOKINES AND MITOGENS TO INHIBIT PATHOLOGICAL IMMUNE RESPONSES

(75) Inventor: David A. Horwitz, Santa Monica, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 09/186,771

(22) Filed: Nov. 5, 1998

Related U.S. Application Data

(60) Provisional application No. 60/064,507, filed on Nov. 5, 1997.

(51) Int. Cl.$^7$ .................................................. A61K 45/00
(52) U.S. Cl. ........................................ 424/93.71; 424/85.2
(58) Field of Search ................................ 424/93.71, 85.2

(56) References Cited

PUBLICATIONS

Delgiudice, G., et al., "TGF–beta activity is increased in systemic lupus erythematosus (SLE) and progressive systemic sclerosis (PSS)", *Hospital Special Surgery*, Arthritis and Rheumatism 36 vol. 36 (9 Suppl.) (Sep. 1993).

Gray, J.D., et al., "The Role of Transforming Growth Factor β in the Generation of Suppression: An Interaction between CD8$^+$ T and NK Cells", *J. Exp. Med.*, vol. 180 1937–1942 (Nov. 1994).

Gray, J. D., et al., "Generation of an Inhibitory Circuit Involving CD8$^+$ T Cells, IL–2, and NK Cell–Derived TGF–β: Contrasting Effects of Anti–CD2 and Anti–CD3", *The Amer. Assn. of Immunol.*, 2250–2254 (1998).

Horwitz, D. A., et al., "The immunoregulatory effects of NK cells: the role of TGF–β and implications for autoimmunity", vol. 18(11):538–542 (Nov. 1997). *Immunology Today*.

Huggins, M. L., et al., "Modulation of the Autoimmune Response in Lupus Mice by Oral Administration of Attenuated *Salmonella typhimurium* Expressing the IL–2 and TGF–β Genes", *Annals of New York Acad. of Sciences*, vol. 815:499–502 (1997).

Ohtsuka, K., et al., "Decreased Production of TGF–β by Lymphocytes from Patients with Systemic Lupus Erythematosus", 2539–2545 (1998). *The Journal of Immunology*.

Fernandes, G., et al., "Calorie restriction delays autoimmune murine lupus by differentially modulating oncogenes and TGF–beta–1 expression", 848 (1995). 9th International Congress on Immuno.

Chandrasekar, B., et al., "Dietary calorie restriction inhibits transforming growth factor–beta (TGF–beta) expression in murine lupus nephritis", 848 (1995). 9th International Congress on Immunol.

Gray et al., "Activated Natural Killer Cells Can Induce Resting B Cells to Produce Immunoglobulin," *Arthritis & Rheumatism*, 37(9)suppl:S378 (1994).

Chavin et al., "Anti–CD2 mAbs Suppress Cytotoxic Lymphocyte Activity by the Generation of Th2 Suppressor Cells and Receptor Blockade," *Journal of Immunology* 152:3729–3739 (1994).

*Primary Examiner*—Francisco Prats
*Assistant Examiner*—Susan D. Coe
(74) *Attorney, Agent, or Firm*—Flehr Hohbach Test Albritton & Herbert LLP

(57) ABSTRACT

A method for treating autoimmune disease by removing peripheral blood mononuclear cells from a patient, treating the mononuclear cells with an inhibitory composition that suppresses immunoglobulin production, and reintroducing the treated cells to the patient. The inhibitory composition can be IL-2, TGF-β, or a CD2 activator.

5 Claims, 4 Drawing Sheets

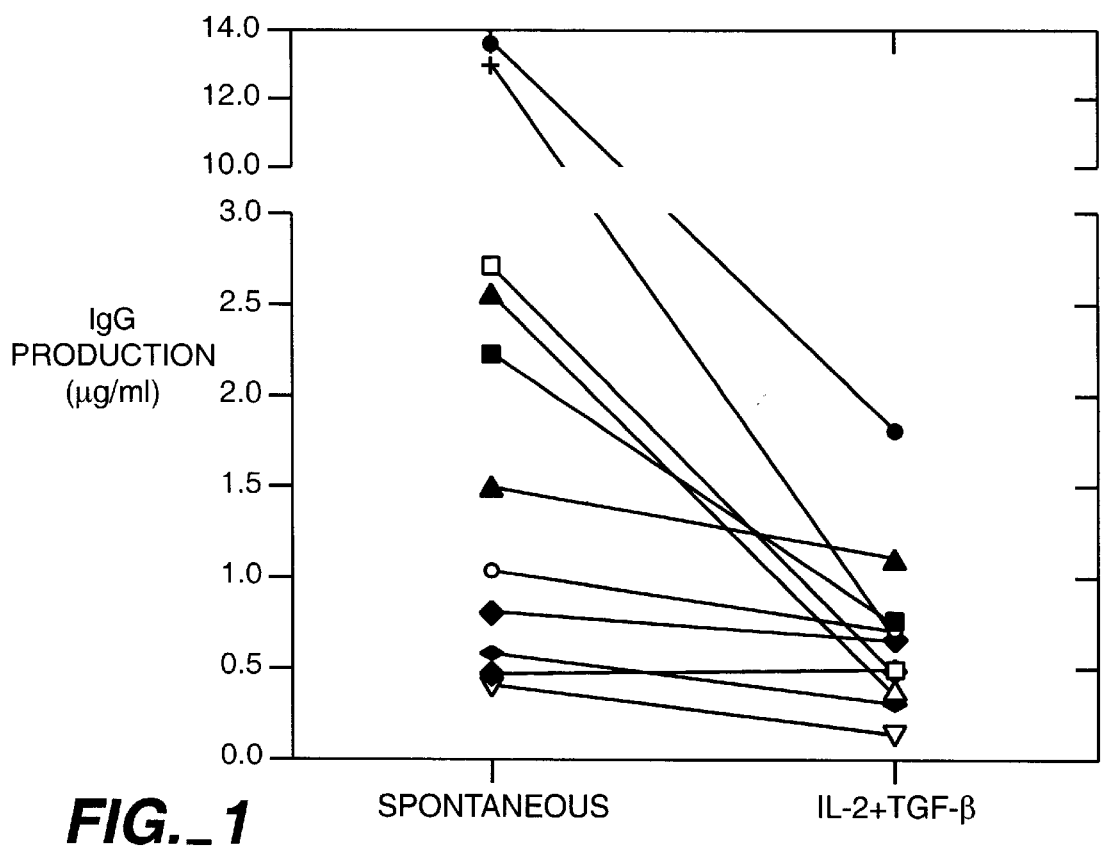
FIG._1
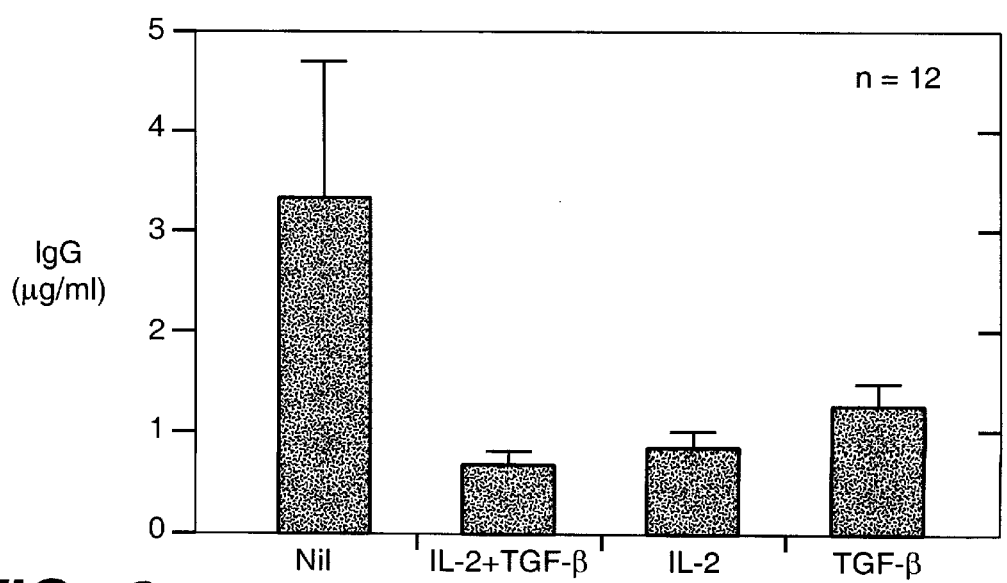
FIG._2

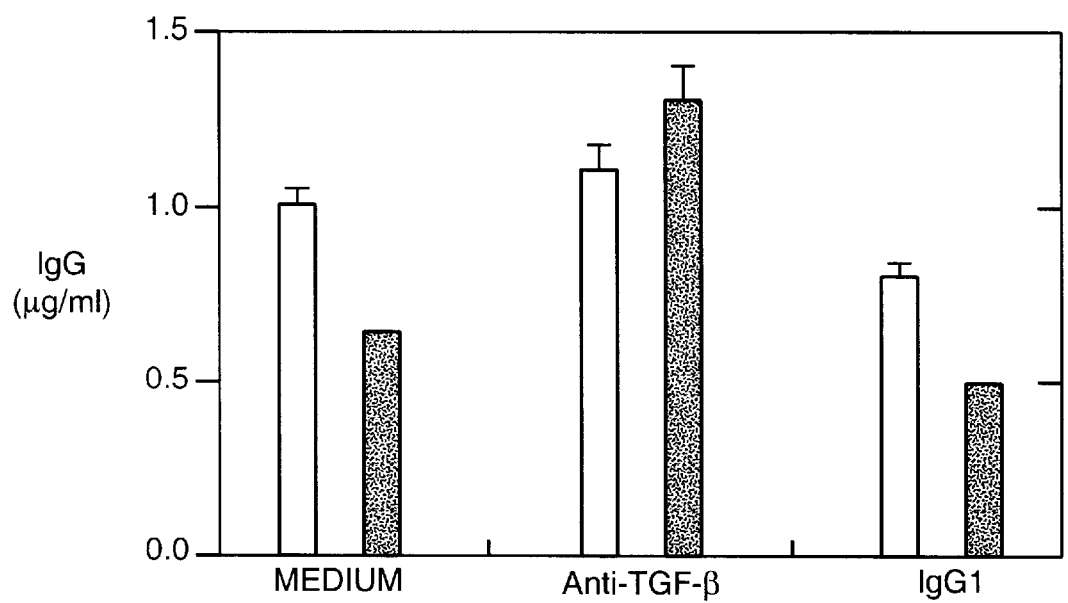
FIG._3A
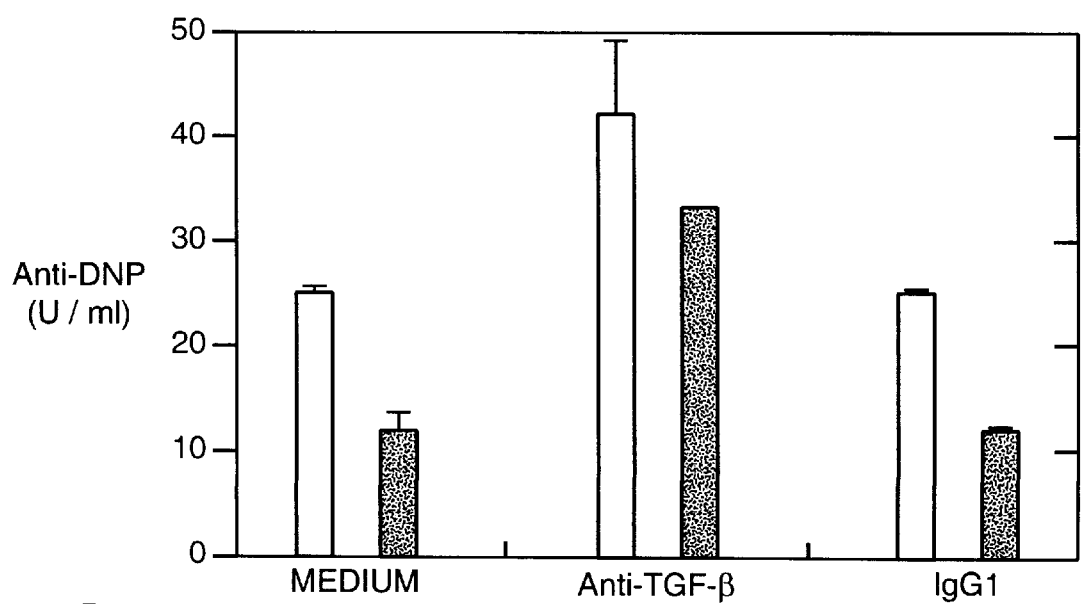
FIG._3B

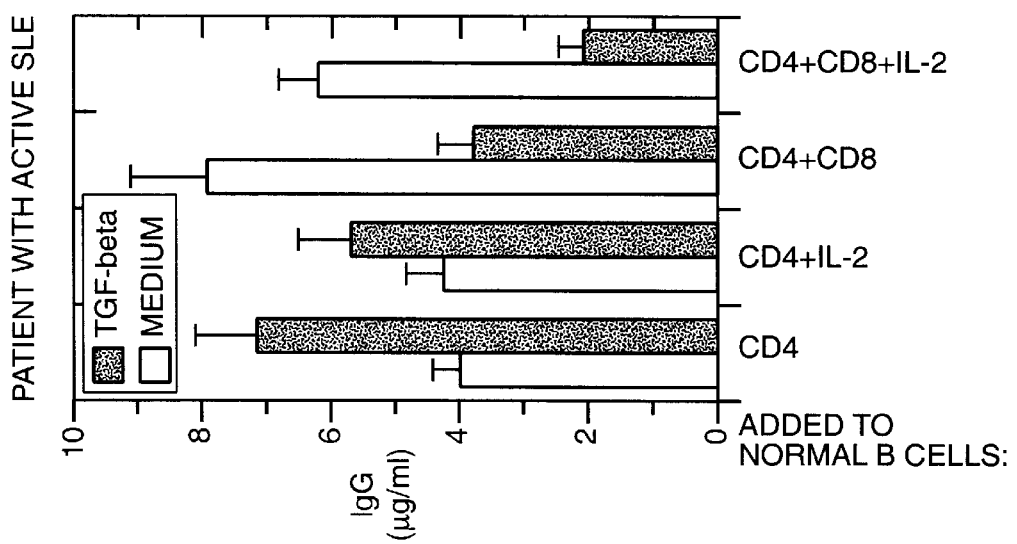
FIG._4C
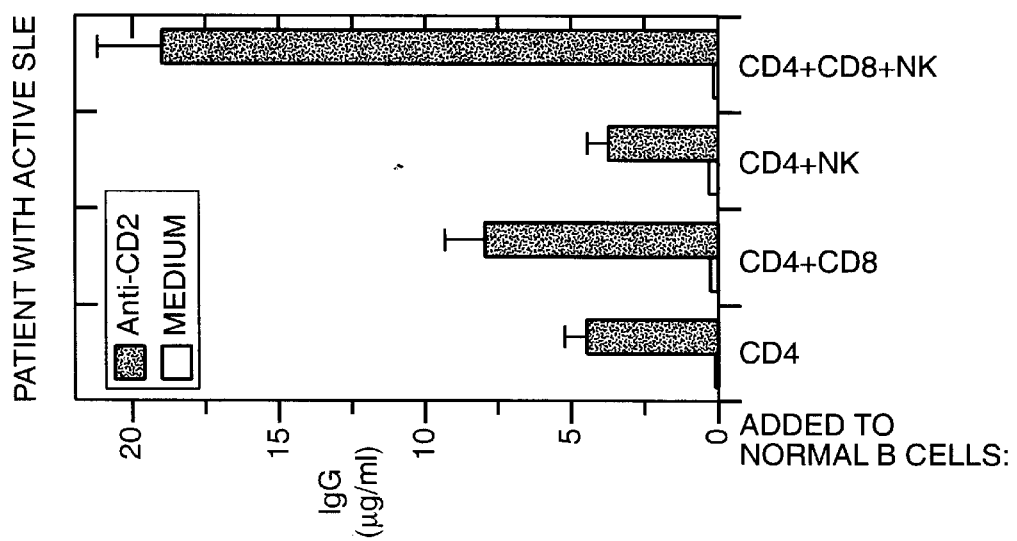
FIG._4B
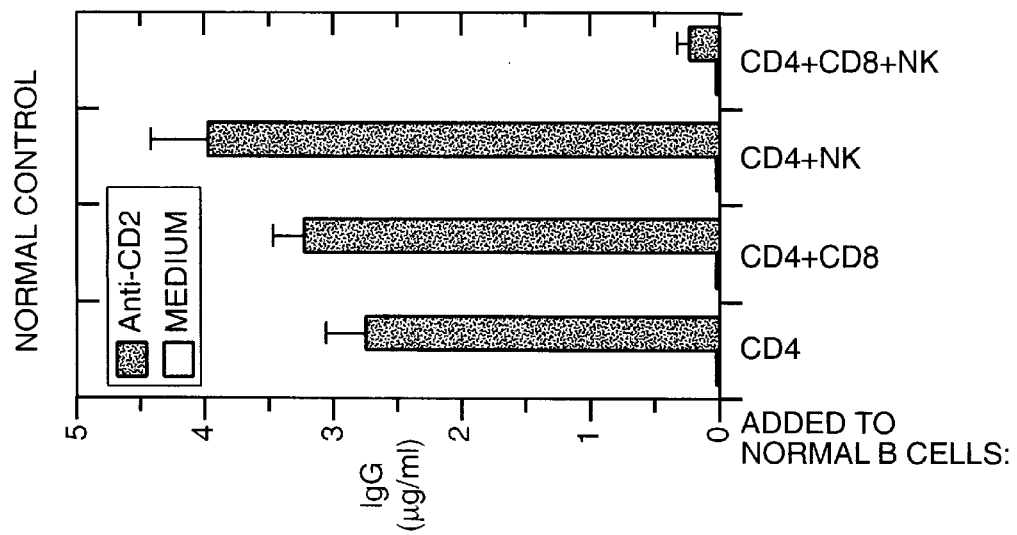
FIG._4A

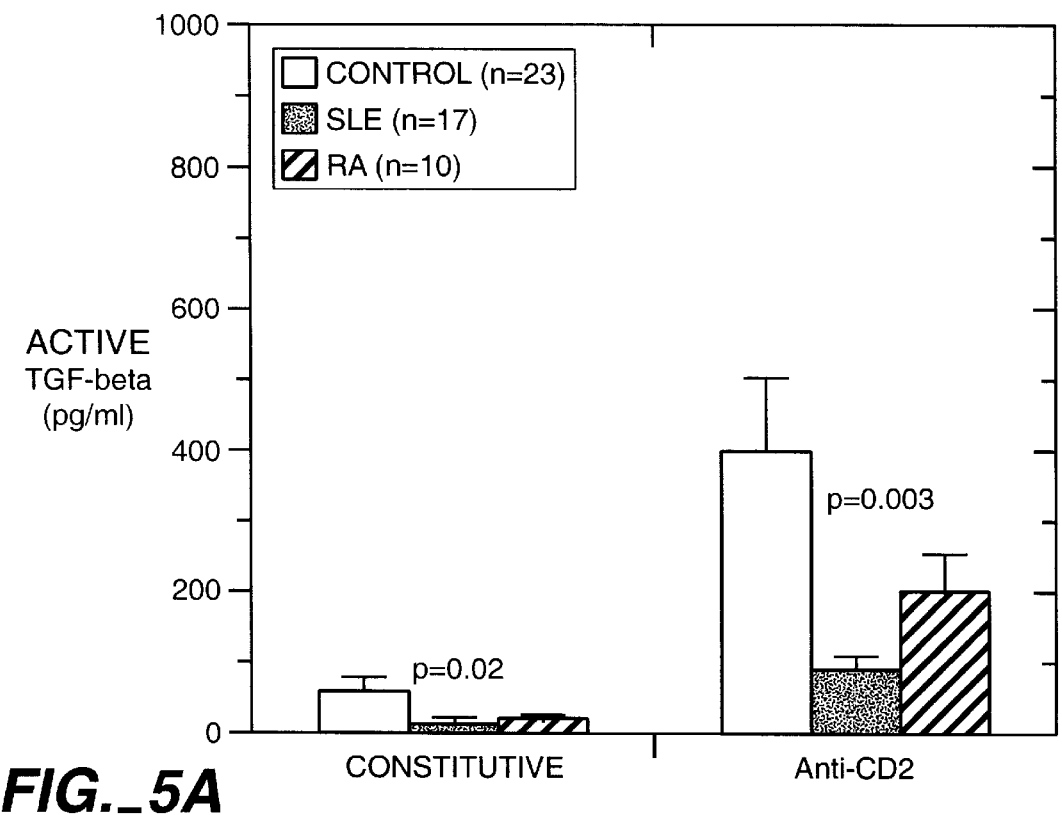
FIG._5A
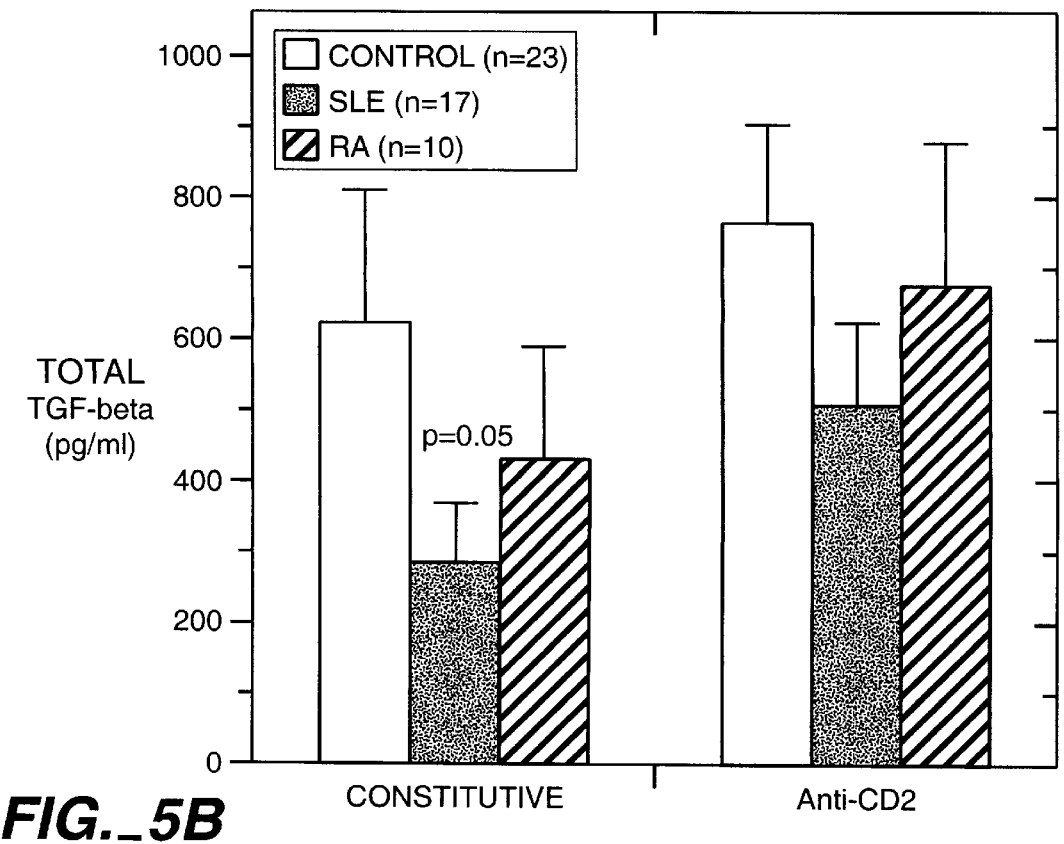
FIG._5B

USE OF CYTOKINES AND MITOGENS TO INHIBIT PATHOLOGICAL IMMUNE RESPONSES

This application claims benefit of Provisional Application 60/064,507 filed Nov. 5, 1997.

FIELD OF THE INVENTION

The field of the invention is generally related to methods of treating antibody-mediated autoimmune diseases.

BACKGROUND OF THE INVENTION

Autoimmune diseases are caused by the failure of the immune system to distinguish self from non-self. In these diseases, the immune system reacts against self tissues and this response ultimately causes inflammation and tissue injury. Autoimmune diseases can be classified into two basic categories: antibody-mediated diseases such as systemic lupus erythematosus (SLE), pemphigus vulgaris, myasthenia gravis, hemolytic anemia, thrombocytopenia purpura, Grave's disease, Sjogren 's disease and dermatomyositis; and cell-mediated diseases such as Hashimoto's disease, polymyositis, disease inflammatory bowel disease, multiple sclerosis, diabetes mellitus, rheumatoid arthritis, and scleroderma.

In many autoimmune diseases, tissue injury is caused by the production of antibodies to native tissue. These antibodies are called autoantibodies, in that they are produced by a mammal and have binding sites to the mammals own tissue. Some of these disorders have characteristic waxing and waning of the amount of autobodies circulating causing varying symptoms over time.

Of the different types of antibody-mediated autoimmune disorders, SLE is a disorder that has been well studied and documented. SLE is a disorder of generalized autoimmunity characterized by B cell hyperactivity with numerous autoantibodies against nuclear, cytoplasmic and cell surface antigens. This autoimmune disease has a multifactorial pathogenesis with genetic and environmental precipitating factors (reviewed in Hahn, B. H., *Dubois' Lupus Erythematosus*, 5th Ed. (1997), pp. 69–76 (D. J. Wallace et al. eds., Williams and Wilkins, Baltimore)). Among the numerous lymphocyte defects described in SLE is a failure of regulatory T cells to inhibit B cell function (Horwitz, D. A., Dubois' Lupus Erythematosus, 5th Ed. (1997), pp. 155–194 (D. J. Wallace et al. eds., Williams and Wilkins, Baltimore)). Regulatory T cells can down-regulate antibody synthesis by lytic or cytokine-mediated mechanisms. The latter involve transforming growth factor-beta (TGFβ) and other inhibitory cytokines (Wahl, S. M. (1994), *J Exp Med* 180:1587–190). Circulating B lymphocytes spontaneously secreting Ig are increased in patients with active SLE (Klinman, D. M. et al. (1991), *Arthritis Rheum* 34:1404–1410). Sustained production of polyclonal IgG and autoantibodies in vitro requires T cell help (Shivakumar, S. et al. (1989), *J Immunol* 143:103–112).

Clinical manifestations of SLE include a rash (especially on the face in a "butterfly" distribution), glomerulonephritis, pleurisy, pericarditis and central nervous system involvement. Most patients are women, and are relatively young (average age at diagnosis is 29).

The treatment of SLE depends on the clinical manifestations. Some patients with mild clinical symptoms respond to simple measures such as nonsteroidal anti-inflammatory agents. However, more severe symptoms usually require steroids with potent anti-inflammatory and immunosuppressive action such as prednisone. Other strong immunosuppressive drugs which can be used are azathioprine and cyclophosphamide. The steroids and other immunosuppressive drugs have side effects due to the global reduction of the mammal's immune system. There is presently no ideal treatment for SLE and the disease cannot be cured.

Currently, considerable attention has been focused on the identity of genes which enhance the susceptibility or resistance to SLE, the identification of antigenic determinants that trigger the disease, the molecular mechanisms of T cell activation which results in survival or apoptosis, cytokines which determine T cell function, and the properties of the autoantibody-forming B cells. Many examples of T cell dysregulation in SLE have been described (reviewed in Horwitz, D. A. et al., *Dubois' Lupus Erythematosus*, 5th Ed. (1997), pp. 83–96 (D. J. Wallace et al. eds., Williams and Wilkins, Baltimore). Although it is well recognized that the primary role of certain lymphocytes is to down-regulate immune responses, progress in elucidating the identity and mechanisms required for generation of these cells has been slow.

Interleukin-2 (IL-2) has previously been considered to have an important role in the generation of antigen non-specific T suppressor cells. Anti-IL-2 antibodies given to mice coincident with the induction of graft-versus-host-disease resulted in several features of SLE (Via, C. S. et al. (1993), *International Immunol.* 5:565–572). Whether IL-2 directly or indirectly is important in the generation of suppression has been controversial (Fast, L. D. (1992), *J. Immunol.* 149:1510–1515; Hirohata, S. et al. (1989), *J. Immunol.* 142:3104–3112; Baylor, C. E. (1992), *Advances Exp. Med. Biol.* 319:125–135). Recently, IL-2 has been shown to induce CD8+ cells to suppress HIV replication in CD4+ T cells by a non-lytic mechanism. This effect is cytokine mediated, but the specific cytokine has not been identified (Kinter, A. L. et al. *Proc. Natl. Acad. Sci. USA* 92:10985–10989; Barker, T. D. et al. (1996), *J. Immunol.* 156:4478–4483). T cell production of IL-2 is decreased in SLE (Horwitz, D. A. et al. (1997), *Dubois' Lupus Erythematosus,* 5th Ed. (1997), pp. 83–96, D. J. Wallace et al. eds., Williams and Wilkins, Baltimore).

CD8+ T cells from subjects with SLE sustain rather than suppress polyclonal IgG production (Linker-Israeli, M. et al. (1990), *Arthritis Rheum.* 33:1216–1225). CD8+ T cells from healthy donors can be stimulated to enhance Ig production (Takahashi, T. et al. (1991), *Clin. Immunol. Immunopath.* 58:352–365). However, neither IL-2 nor CD4+ T cells, by themselves, were found to induce CD8+ T cells to develop strong suppressive activity. When NK cells were included in the cultures, strong suppressive activity appeared (Gray, J. D. et al. (1994) *J. Exp. Med.* 180:1937–1942). It is believed that the contribution of NK cells in the culture was to produce transforming growth factor beta (TGFβ) in its active form. It was then discovered that non-immunosuppressive (2–10 pg/ml) concentrations of this cytokine served as a co-factor for the generation of strong suppressive effects on IgG and IgM production (Gray, J. D. et al. (1994) *J. Exp. Med.* 180:1937–1942). In addition, it is believed that NK cells are the principal source of TGFβ in unstimulated lymphocytes (Gray, J. D. et al. (1998), *J. Immunol.* 160:2248–2254).

TGFβ is a multifunctional family of cytokines important in tissue repair, inflammation and immunoregulation (Massague, J. (1980), *Ann. Rev. Cell Biol.* 6:597). TGFβ is unlike most other cytokines in that the protein released is biologically inactive and unable to bind to specific receptors (Sporn, M. B. et al. (1987) *J. Cell Biol.* 105:1039–1045).

The latent complex is cleaved extracelluarly to release active cytokine as discussed below. The response to TGFβ requires the interaction of two surface receptors (TGFβ-R1) and TGFβ-R2) which are ubiquitously found on mononuclear cells (Massague, J. (1992), *Cell* 69:1067–1070). Thus, the conversion of latent to active TGFβ is the critical step which determines the biological effects of this cytokine.

It was found that SLE patients have decreased production of TGFβ by NK cells. Defects in constitutive TGFβ produced by NK cells as well as induced TGFβ were documented in a study of 38 SLE patients (Ohtsuka, K. et al. (1998), *J. Immunol.* 160:2539–2545). Interestingly, the addition of neither recombinant IL-2 nor TNF-alpha, nor antagonism of IL-10 could not normalize the TGFβ defect in SLE. Decreased production of TGFβ in SLE did not correlate with activity of disease and, therefore, may be a primary defect.

Systemic administration of Treating a SLE patient with systemic TGFβ, IL-2, or a combination of both can lead to serious side effects. These cytokines have numerous effects on different body tissues and are not very safe to deliver to a patient systemically. It is, therefore, an object of the invention to provide methods and kits for treating mammalian cells that are responsible for controlling the regulation of autoantibodies to increase the population of cells that down regulate auto-antibody production.

SUMMARY OF THE INVENTION

In accordance with the objects outlined herein, the present invention provides methods for inhibiting Ig production in a sample of ex vivo peripheral blood mononuclear cells (PBMCs) comprising adding an inhibitory composition to the cell population.

In an additional aspect, the present invention provides methods for treating an autoimmune disorder in a patient. The methods comprise removing peripheral blood mononuclear cells (PBMC) from the patient and treating the cells with an inhibitory composition for a time sufficient to suppress Ig production or stimulate or induce cells to down regulate Ig production. The cells are then reintroduced to the patient, with a resulting amelioration of the autoimmune symptoms. The inhibitory composition preferably comprises a combination of IL-2 and TGF-β.

In an additional aspect, the invention provides kits for the treatment of an autoimmune disorder in a patient. The kits comprise a cell treatment container adapted to receive cells from a patient with an antibody-mediated autoimmune disorder and at least one dose of an inhibitory composition.

BRIEF DESCRIPTION OF THE DRAWINGS

FIG. 1 shows that incubation of SLE patients PBMC with IL-2 and TGF-β decreases spontaneous immunoglobulin production. PBMC ($2\times10^5$/well) were cultured in AIM-V serum free medium with or without IL-2 (10U/ml) and TGF-β (10pg/ml). After 3 days, the wells were washed three times and fresh AIM-V medium added. Supernatants were collected from the wells after a further 7 days and IgG content determined by an ELISA.

FIG. 2 shows that both IL-2 and TGF-β significantly decrease spontaneous IgG production. The values represent the mean ± SEM of IgG ($\mu$g/ml) produced by the 12 SLE patients PBMC cultured as described in legend to FIG. 1 except some cells were also incubated with IL-2 (10U/ml) or TGF-β (10pg/ml) only.

FIGS. 3A and 3B show that anti-TGF-β can reverse the effects of IL-2. SLE patients PBMC was cultured for three days in the presence (solid bars) or absence (spotted bars) of IL-2 (10U/ml). Included in these cultures was medium, anti-TGF-β (10$\mu$g/ml) or control mouse IgG1 (10$\mu$g/ml). After 3 days the wells were washed and fresh AIM-V medium added. Supernatants were collected after a further seven days and assayed for IgG (FIG. 3A) or anti-NP (FIG. 3B) content by an ELISA.

FIGS. 4A, 4B and 4C depict regulatory effects of DC8+ T cells on antibody production. (A) Synergism between NK cells and CD8+ cells in the suppression of IgG production in a healthy subject. CD4+ cells and B cells were stimulated with anti-CD2 and the effects of CD8+ cells and NK cells were examined. The combination of NK and CD8+ cells markedly inhibited anti-CD2 induced IgG production we previously reported (Gray, J. D. et al. (1998), *J Immunol* 160:2248–2254; Gray, J. D. et al. (1994), *J Exp Med* 180:1937–1942). (B) NK cells and CD8+ cells enhance IgG synthesis in SLE. CD4+ cells from a patient with active SLE and resting B cells from a healthy subject were stimulated with anti-CD2. Enhancement of IgG production by SLE CD8+ cells was markedly increased by the addition of NK cells. (C) Cytokine normalization of CD8+ T cell function in SLE. In parallel with the study shown in FIG. 4B, CD4+ T cells from this patient were stimulated with anti-CD2 in the presence or absence of CD8+ T cells. IL-2 (1OU/ml) and/or TGF-β (2pg/ml) was added where indicated. These cytokines abolished the helper effects of these CD8+ cells and enabled them to inhibit IgG production by 75%.

FIG. 5 depicts the lymphocyte production of TGF-β1 by unstimulated and anti-CD2 stimulated cells. PBL from healthy donors and patients of SLE and RA were added to microtiter plates at $1\times10^5$/well. Some wells received the anti-CD2 mAbs GT2 (1:40) and T11 (1:80). After 2 days at 37° C., supernatants were harvested and assayed for active and total TGF-β1. Significant p values are indicated.

DETAILED DESCRIPTION

The present invention is directed to methods of treating antibody-mediated autoimmune disorders, such as systemic lupus erythematosus (SLE), by removing cells from a patient and treating them with a composition that will down-regulate B cell hyperactivity and thus inhibit the production of Ig antibodies, including autoantibodies, to ameliorate the symptoms of the autoimmune disorder. This strategy is unlike almost all other treatment modalities currently in use which are either anti-inflammatory or immunosuppressive. Commonly used corticosteroids suppress cytokine production and block the terminal events which cause tissue injury, but generally do not alter the underlying autoimmune response. Cytotoxic drugs or experimental genetically engineered biologicals such as monoclonal antibodies may also deplete specific lymphocyte populations or interfere with their function. These drugs are generally only moderately successful and have severe adverse side effects. Certain cytokines have been given systemically to patients, but these agents also have broad actions with associated serious adverse side effects.

By contrast, the strategy of the present invention is to produce remission by restoring normal regulatory cell function and, thus, "resetting" the immune system. Another significant potential advantage of this strategy is a low probability of serious adverse side effects. Since only trace amounts of inhibitory compositions such as cytokines will be returned to the patient, there should be minimal toxicity.

Circulating B lymphocytes spontaneously secreting IgG are increased in patients with active SLE (Blaese, R. M., et al. (1980), *Am J. Med* 69:345–350; Klinman, D. M. et al. (1991) *Arthritis Rheum* 34: 1404–1410). Sustained production of polyclonal IgG and autoantibodies in vitro requires T cell help (Shivakumar, S. et al. (1989), *J Immunol* 143:103–112). Previous studies of T cell regulation of spontaneous IgG production shows that while CD8+ T cells inhibit antibody production in healthy individuals, in SLE these cells support B cell function instead (Linker-Israeli, M. et al. (1990), *Arthritis Rheum* 33:1216–1225).

Accordingly, the present invention is drawn to methods of treating antibody-mediated autoimmune diseases that comprise removing peripheral blood mononuclear cells (PBMCs) from the patient with the autoimmune disease and treating the cells with an inhibitory composition.

Without being bound by theory, it appears that there are several ways the methods of the invention may work. First of all, the treatment of the cells by an inhibitory composition leads to the direct suppression of Ig production in the treated cells, which can lead to amelioration of autoimmune symptoms. Alternatively or additionally, the treatment of the cells induces regulatory cells to down regulate Ig production in other cells. Ig in this context includes all forms of Ig, including IgM, IgG, IgE, etc. The net result is a decrease in the amount of Ig in the system.

Thus, the present invention restores the capacity of peripheral blood T cells from patients with autoimmune disorders to down regulate antibody production by treating them with an inhibitory composition ex vivo.

Accordingly, the present invention provides methods of treating antibody-mediated autoimmune disorders in a patient. By "antibody-mediated autoimmune diseases" herein is meant a disease in which individuals develop antibodies to constituents of their own cells or tissues. Antibody-mediated autoimmune diseases include, but are not limited to, systemic lupus erythematosus (SLE), pemphigus vulgaris, myasthenia gravis, hemolytic anemia, thrombocytopenia purpura, Grave's disease, dermatomyositis and Sjogren's disease. The preferred autoimmune disease for treatment using the methods of the invention is SLE.

By "treating" an autoimmune disorder herein is meant that at least one symptom of the autoimmune disorder is ameliorated by the methods outlined herein. This may be evaluated in a number of ways, including both objective and subjective factors on the part of the patient. For example, immunological manifestations of disease can be evaluated; for example, the level of spontaneous Ig antibody and autoantibody production, particularly IgG production in the case of SLE, is reduced. Total Ig antibody levels may be measured, or autoantibodies, including, but not limited to, anti-double-stranded DNA (ds DNA) antibodies, anti-nucleoprotein antibodies, anti-Sm, anti-Rho, and anti-La. Physical symptoms may be altered, such as the disappearance or reduction in a rash in SLE. Renal function tests may be performed to determine alterations; laboratory evidence of tissue damage relating to inflammation may be evaluated. Decreased levels of circulating immune complexes and levels of serum complement are further evidence of improvement. In the case of SLE, a lessening of anemia may be seen. The ability to decrease a patient's otherwise required drugs such as immunosuppressives can also be an indication of successful treatment. Other evaluations of successful treatment will be apparent to those of skill in the art of the particular autoimmune disease.

By "patient" herein is meant a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

The methods provide for the removal of blood cells from a patient. In general, peripheral blood mononuclear cells (PBMCs) are taken from a patient using standard techniques. By "peripheral blood mononuclear cells" or "PBMCs" herein is meant lymphocytes (including T-cells, B-cells, NK cells, etc.) and monocytes. As outlined more fully below, it appears that the main effect of the inhibitory composition is to enable CD8+ T cells to suppress IgG production. Accordingly, the PBMC population should comprise CD8+ T cells. Preferably, only PBMCs are taken, either leaving or returning substantially all of the red blood cells and polymorphonuclear leukocytes to the patient. This is done as is known in the art, for example using leukophoresis techniques. In general, a 5 to 7 liter leukophoresis step is done, which essentially removes PBMCs from a patient, returning the remaining blood components. Collection of the cell sample is preferably done in the presence of an anticoagulant such as heparin, as is known in the art.

In general, the sample comprising the PBMCs can be pretreated in a wide variety of ways. Generally, once collected, the cells can be additionally concentrated, if this was not done simultaneously with collection or to further purify and/or concentrate the cells. The cells may be washed, counted, and resuspended in buffer.

The PBMCs are generally concentrated for treatment, using standard techniques in the art. In a preferred embodiment, the leukophoresis collection step results a concentrated sample of PBMCs, in a sterile leukopak, that may contain reagents and/or doses of the inhibitory composition, as is more fully outlined below. Generally, an additional concentration/purification step is done, such as Ficoll-Hypaque density gradient centrifugation as is known in the art.

In a preferred embodiment, the PBMCs are then washed to remove serum proteins and soluble blood components, such as autoantibodies, inhibitors, etc., using techniques well known in the art. Generally, this involves addition of physiological media or buffer, followed by centrifugation. This may be repeated as necessary. They can be resuspended in physiological media, preferably AIM-V serum free medium (Life Technologies) (since serum contains significant amounts of inhibitors) although buffers such as Hanks balanced salt solution (HBBS) or physiological buffered saline (PBS) can also be used.

Generally, the cells are then counted; in general from $1 \times 10^9$ to $2 \times 10^9$ white blood cells are collected from a 5–7 liter leukophoresis step. These cells are brought up roughly 200 mls of buffer or media.

In a preferred embodiment, the PBMCs may be enriched for one or more cell types. For example, the PBMCs may be enriched for CD8+ T cells or CD4+ T cells. This is done as is known in the art, as described in Gray et al. (1998), *J. Immunol.* 160:2248, hereby incorporated by reference. Generally, this is done using commercially available immunoabsorbent columns, or using research procedures (the PBMCs are added to a nylon wool column and the eluted, nonadherent cells are treated with antibodies to CD4, CD16, CD11b and CD74, followed by treatment with immunomagnetic beads, leaving a population enriched for CD8+ T cells).

Once the cells have undergone any necessary pretreatment, the cells are treated with an inhibitory composition. By "treated" herein is meant that the cells are incubated with the inhibitory composition for a time period sufficient to develop the capacity to inhibit Ig and autoantibody production, particularly when transferred back to the patient. The incubation will generally be under physiological temperature. As noted above, this may happen as a result of direct suppression of Ig production by the treated cells, or by inducing regulatory cells to down regulate the production of Ig in the patient's lymphoid organs.

By "inhibitory composition" or "Ig production inhibitor composition" or "humoral inhibitor composition" herein is meant a composition that can cause inhibition of spontaneous Ig and autoantibody production. Generally, these compositions are cytokines. Suitable inhibitory compositions include, but are not limited to, IL-2, TGF-β, and CD2 activators, including anti-CD2 antibodies and the CD2 ligand, LFA-3, as well as mixtures or combinations of these. A preferred inhibitory composition is a mixture of IL-2 and TGF-β.

The concentration of the inhibitory composition will vary on the identity of the composition. In a preferred embodiment, TFG-β is used as the inhibitory composition. By "transforming growth factor -β" or "TGF-β" herein is meant any one of the family of the TGF-βs, including the three isoforms TGF-β1, TGF-β2, and TGF-β3; see Massague, J. (1980), *J. Ann. Rev. Cell Biol* 6:597. Lymphocytes and monocytes produce the β1 isoform of this cytokine (Kehrl, J. H. et al. (1991), *Int J Cell Cloning* 9: 438–450). The TFG-β can be any form of TFG-β that is active on the mammalian cells being treated. In humans, recombinant TFG-β is currently preferred. A preferred human TGF-β can be purchased from Genzyme Pharmaceuticals, Farmington, Mass., In general, the concentration of TGF-β used ranges from about 2 picograms/ml of cell suspension to about 2 nanograms, with from about 10 pg to about 500 pg being preferred, and from about 50 pg to about 150 pg being especially preferred, and 100 pg being ideal.

In a preferred embodiment, IL-2 is used as the inhibitory composition. The IL-2 can be any form of IL-2 that is active on the mammalian cells being treated. In humans, recombinant IL-2 is currently preferred. Recombinant human IL-2 can be purchased from Cetus, Emeryville, Calif. In general, the concentration of IL-2 used ranges from about 1 Unit/ml of cell suspension to about 100 U/ml, with from about 5 U/ml to about 25 U/ml being preferred, and with 10 U/ml being especially preferred. In a preferred embodiment, IL-2 is not used alone.

In a preferred embodiment, a CD2 activator such as anti CD2 antibodies or the CD2 ligand LFA-3 are used as the inhibitory composition. CD2 is a cell surface glycoprotein expressed by T lymphocytes. By "CD2 activator" herein is meant compound that will initiate the CD2 signaling pathway. A preferred CD2 activator comprises anti CD2 antibodies (OKT11, American Type Culture Collection, Rockville Md.). In general, the concentration of CD2 activator used will be sufficient to induce the production of TGF-β. The concentration of anti CD2 antibodies used ranges from about 1 ng/ml to about 10 μg/ml, with from about 10 ng/ml to about 100 ng/ml being especially preferred.

In addition to treatment with an inhibitory composition, in some embodiments it is desirable to use a mitogen to activate the cells; that is, many resting phase cells do not contain large amounts of cytokine receptors. The use of a mitogen such as Concanavalin A can allow the stimulation of the cells to produce cytokine receptors, which in turn makes the methods of the invention more effective. When a mitogen such as ConA is used, it is generally used as is known in the art, at concentrations ranging from 1 μg/ml to about 10 μg/ml is used. In addition, it may be desirable to wash the cells with components to remove the ConA, such as α-methyl mannoside, as is known in the art.

The inhibitory composition is incubated with the cells for a period of time sufficient to cause an effect. In a preferred embodiment, treatment of the cells with the inhibitory composition is followed by immediate transplantation back into the patient. Accordingly, in a preferred embodiment, the cells are incubated with the inhibitory composition for from about 12 to about 120 hours, with from about 24 to about 72 hours being preferred, and 48 hours being particularly preferred.

In one embodiment, the cells are treated for a period of time, washed to remove the inhibitory composition, and may be reincubated. Before introduction into the patient, the cells are preferably washed as outlined herein to remove the inhibitory composition. Further incubations for testing or evaluation may also be done, ranging in time from a few hours to several days. If evaluation of Ig production prior to introduction to a patient is desirable, the cells will be incubated for several days to allow Ig production (or lack thereof) to occur.

Once the cells have been treated, they may be evaluated or tested prior to autotransplantation back into the patient. For example, a sample may be removed to do: sterility testing; gram staining, microbiological studies; LAL studies; mycoplasma studies; flow cytometry to identify cell types; functional studies, etc. Similarly, these and other lymphocyte studies may be done both before and after treatment.

In a preferred embodiment, the quantity or quality, i.e. type, of Ig production, may be evaluated. Thus, for example, the total levels of Ig may be evaluated, or the levels of specific types of Igs, for example, IgG, IgM, etc.; IgG anti-DNA autoantibodies, anti-nucleoprotein (NP) antibodies, etc.

In a preferred embodiment, the levels of Ig, particularly IgG, are tested using well known techniques, including ELISA assays, as described in Abo et al. (1987), *Clin. Exp. Immunol.* 67:544 and Linker-Israeli et al. (1990), *Arthritis Rheum* 33:1216, both of which are hereby expressly incorporated by reference. These techniques may also be used to detect the levels of specific antibodies, such as autoantibodies.

In a preferred embodiment, the treatment results in a significant decrease in the amount of IgG and autoantibodies produced, with a decrease of at least 10% being preferred, at least 25% being especially preferred, and at least 50% being particularly preferred. In many embodiments, decreases of 75% or greater are seen.

In a preferred embodiment, prior to transplantation, the amount of total or active TGF-β can also be tested. As noted herein, TGF-β is made as a latent precursor that is activated post-translationally.

After the treatment, the cells are transplanted or reintroduced back into the patient. This is generally done as is known in the art, and usually comprises injecting or introducing the treated cells back into the patient, via intravenous administration, as will be appreciated by those in the art. For example, the cells may be placed in a 50 ml Fenwall infusion bag by injection using sterile syringes or other sterile transfer mechanisms. The cells can then be immediately infused via IV administration over a period of time, such as 15 minutes, into a free flow IV line into the patient. In some embodiments, additional reagents such as buffers or salts may be added as well.

After reintroducing the cells into the patient, the effect of the treatment may be evaluated, if desired, as is generally outlined above. Thus, evaluating immunological manifestations of the disease may be done; for example the titers of total Ig or of specific immunoglobulins, renal function tests, tissue damage evaluation, etc. may be done.

The treatment may be repeated as needed or required. For example, the treatment may be done once a week for a period of weeks, or multiple times a week for a period of time, for example 3–5 times over a two week period. Generally, the amelioration of the autoimmune disease symptoms persists for some period of time, preferably at least months. Over time, the patient may experience a relapse of symptoms, at which point the treatments may be repeated.

In a preferred embodiment, the invention further provides kits for the practice of the methods of the invention, i.e., the incubation of the cells with the inhibitory compositions. The kit may have a number of components. The kit comprises a cell treatment container that is adapted to receive cells from a patient with an antibody-mediated autoimmune disorder. The container should be sterile. In some embodiments, the cell treatment container is used for collection of the cells, for example it is adaptable to be hooked up to a leukophoresis machine using an inlet port. In other embodiments, a separate cell collection container may be used.

The form and composition of the cell treatment container may vary, as will be appreciated by those in the art. Generally the container may be in a number of different forms, including a flexible bag, similar to an IV bag, or a rigid container similar to a cell culture vessel. It may be configured to allow stirring. Generally, the composition of the container will be any suitable, biologically inert material, such as glass or plastic, including polypropylene, polyethylene, etc. The cell treatment container may have one or more inlet or outlet ports, for the introduction or removal of cells, reagents, inhibitory compositions, etc. For example, the container may comprise a sampling port for the removal of a fraction of the cells for analysis prior to reintroduction into the patient. Similarly, the container may comprise an exit port to allow introduction of the cells into the patient; for example, the container may comprise an adapter for attachment to an IV setup.

The kit further comprises at least one dose of an inhibitory composition. "Dose" in this context means an amount of the inhibitory composition such as cytokines, that is sufficient to cause an effect. In some cases, multiple doses may be included. In one embodiment, the dose may be added to the cell treatment container using a port; alternatively, in a preferred embodiment, the dose is already present in the cell treatment container. In a preferred embodiment, the dose is in a lyophilized form for stability, that can be reconstituted using the cell media, or other reagents.

In some embodiments, the kit may additionally comprise at least one reagent, including buffers, salts, media, proteins, drugs, etc. For example, mitogens can be included. In some embodiments, the kit may additional comprise written instructions for using the kits.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

EXAMPLES

Example 1

Treatment of PBMCs with a Mixture of IL-2 and TFG-β

Example 1 shows that the relatively brief treatment of PBMCs from SLE patients with IL-2 and TFG-β can result in the marked inhibition of spontaneous polyclonal IgG and autoantibody production. As discussed below, PBMC from 12 patients with active SLE were exposed to IL-2 with or without TGF-β for 3 days, washed and cultured seven more days. The mean decrease in IgG secretion was 79%. The strongest inhibitory effect was observed in cases with the most marked B cell hyperactivity. Spontaneous production of anti-nucleoprotein (NP) antibodies was observed in 4 cases and cytokine treatment of PBMC decreased autoantibody production by 50 to 96%. IL-2 inhibited Ig production by either TGF-β-dependent or independent mechanisms in individual patients. In a study of anti-CD2 stimulated IgG production in a patient with active SLE, we documented that IL-2 and TGF-β can reverse the enhancing effects of CD8+ T cells on IgG production and induce suppressive activity instead.

Methods

Study Subjects for Spontaneous Ig Synthesis

Twelve subjects were chosen with a diagnosis of SLE that fulfilled ARA criteria for the classification of SLE (Arnett, F. C. et al. (1998), *Arthritis Rheum* 31: 315–324). These patients were all women, 8 Hispanic, 2 African American, and 2 Asian. The age of each patient and duration of disease is shown in Table 1. Five patients were hospitalized and 7 were outpatients. Those patients who were receiving corticosteroids or antimalarials are also indicated. 8 patients were untreated. Disease activity was assessed with SLAM (Liang, M. H. et al. (1989), *Arthritis Rheum* 32:1107–1118) and SLEDAI (Bombardier, C. et al. (1992), *Arthritis Rheum* 35:630–640) indices with mean values of 16.5 and 13.4 respectively.

TABLE 1

Profile of SLE Patients

| Case | SEX | Age | Ethnicity | Duration | Medications | SLAM | SLEDAI | IgG($\mu$/ml) |
|------|-----|-----|-----------|----------|-------------|------|--------|---------------|
| 1 | F | 18 | AA | 3 yr | Nil | 13 | 9 | 13.7 |
| 2 | F | 37 | H | 6 mo | Nil | 23 | 13 | 13.0 |
| 3 | F | 29 | H | 1 yr | Nil | 15 | 6 | 2.6 |
| 4 | F | 32 | AA | 4 yr | Pred 5 mg Ohchlor 400 mg | 9 | 6 | 2.5 |
| 5 | F | 57 | A | 5 mo | Nil | 24 | 19 | 2.2 |
| 6 | F | 55 | H | 5 mo | Nil | 23 | 22 | 1.5 |
| 7 | F | 27 | H | 3 yr | Pred 20mg Ohchlor 400 mg | 13 | 17 | 1.0 |
| 8 | F | 21 | H | 2 yr | Nil | 18 | 13 | 1.0 |
| 9 | F | 36 | H | 15 yr | Pred 20 mg Ohchlor 400 mg | 14 | 8 | 0.8 |

TABLE 1-continued

Profile of SLE Patients

| Case | SEX | Age | Ethnicity | Duration | Medications | SLAM | SLEDAI | IgG($\mu$/ml) |
|---|---|---|---|---|---|---|---|---|
| 10 | F | 41 | A | 4 yr | Aza 25 mg Nil | 15 | 16 | 0.5 |
| 11 | F | 20 | H | 6 yr | Pred 25 mg | 11 | 16 | 0.4 |
| 12 | F | 25 | H | 1 yr | Nil | 21 | 16 | 0.4 |

Reagents

Recombinant TGF-β and monoclonal anti-TGF-β (1D11.16) antibody, a murine IgG1, were kindly provided by Dr. Bruce Pratt (Genzyme Pharmaceuticals, Farmington, Mass.). Recombinant IL-10 and monoclonal anti-IL-10 (JES3-19F1) antibody, and control rat IgG2a, were kindly provided by Dr. Satwant Narula (Schering Plough Pharmaceuticals, Kenilworth, N.J.). Control murine IgG1 myeloma protein was purchased from Calbiochem, San Diego, Calif. Recombinant human IL-2 was purchased from Chiron, Emmeryville, Calif. Anti-CD2 secreting hybridomas antibodies used OKT11 were obtained from the American Type Culture Collection (ATCC), Rockville, Md. and GT2 was generously provided by A. Bernard, Nice, France). Other antibodies included: anti-CD4 (OKT4, ATCC), anti-CD8 (OKT8, ATCC; CD8, Dako, Carpenteria, Calif.), anti-CD11b (OKM1, ATCC), anti-CD16 (3G8), kindly provided by J. Unkeless, New York, N.Y.); anti-CD20 (Leu 16, Becton Dickinson, San Jose, Calif.) and anti-CD74 (L243, ATCC).

Isolation of Blood Mononuclear Cells

Peripheral blood mononuclear cells (PBMC) were prepared from heparinized venous blood by Ficoll-Hypaque (Pharmacia, Piscataway, N.J.) density gradient centrifugation. The mononuclear cells were washed in PBS with 5mM EDTA (Life Technologies, Grand Island, N.Y.) to remove platelets, which are a rich source of TGF-β.

Cell Culture Procedures

Procedures for cell cultures have been described previously (Wahl, S. M. (1994), *J Exp Med* 180:1587–1590; Gray, J. D. et al. (1998), *J Immunol* 160:2248–2254). In brief, $2 \times 10^5$ of PBMC were cultured in serum-free AIM-V culture medium ( Life Technologies) in the wells of 96-well flat bottom microtiter plate with or without the indicated cytokines. After three days of culture, the PBMC were washed three times then fresh serum-free medium was added. After a further 7 days at 37° C., supernatants were harvested and assayed for total IgG and autoantibodies reactive with calf thymus nucleoprotein (NP) by a solid phase enzyme-linked immunoadsorbant assay (ELISA), as described previously (Linker-Israeli, M. et al. (1990), *Arthritis Rheum* 33:1216–1225). The optical density (OD) readings were transformed into units/ml (U/ml) from a standard curve using positive and negative standards. Supernatants from PBMC culture of SLE patients (with high titers of anti-NP antibodies) and normal individuals were used as controls.

Statistical Analysis

The data were analyzed using Graph Pad, Prism software (San Diego, Calif.). We used analysis of variance (ANOVA) after log transformation of the data and the non-parametric Mann-Whitney test.

Anti-CD2 Induced IgG Synthesis

The effects of CD8+ T cells cultured with or without NK cells on anti-CD2 stimulated CD4+ T cells and B cells was examined in a patient with SLE in a normal control. CD4+ and CD8+ cells were prepared from nylon non-adherent lymphocytes by negative selection using immunomagnetic beads as described previously (Gray, J. D. et al. (1998), *J Immunol* 160:2248–2254). For CD4+ cells the nylon non-adherent cells were stained with antibodies to CD8, CD16, CD11b and CD74. The same antibodies were used to obtain CD8+ cells except that CD4 was substituted for CD8. Purity of CD4+ cells was 95% and CD8+ cells 89%. To obtain NK cells, PBMC were added to a nylon wool column and the eluted, non-adherent cells were immediately rosetted with AET treated sheep red blood cells. The non-rosetting fraction was then stained with anti-CD3 and anti-CD74 (anti-HLA-DR) antibodies and depleted of reacting cells using immunomagnetic beads (Dynal). This resultant population contained 98% CD56+ and <0.5% CD3+ and <0.5% CD20+ lymphocytes. Since SLE B cells spontaneously secrete large amounts of IgG and because of the large amount of blood needed to prepare sufficient numbers of B cells for these studies, we substituted resting B cells from a healthy donor for patient B cells in this study. To obtain B cells, nylon wool adherent cells were immediately rosetted with SRBC to remove any T cells, and treated with 5 mM L-leucine methyl ester for complete removal of monocytes and functional NK cells. The resulting population was >92% CD20+ and <0.5% CD3+.

Results

In 12 patients studied, spontaneous IgG ranged from 0.4 to 13.7 $\mu$g/ml (FIG. 1). Exposure of PBMC to IL-2 ± TGF-β for 72 hours decreased IgG synthesis in 8 of 12 cases studied by at least 50% (mean decrease 79%, p=0.008, Mann Whitney). The most dramatic decreases were observed in cases with the most marked B cell hyperactivity. The correlation between the amount of IgG secreted and percent inhibition by IL-2 and TGF-β was r=0.647, p=0.02.

We compared the effects of IL-2 and TGF-β alone to the combination of IL-2 and TGF-β. FIG. 2 shows that each of these cytokines also inhibited IL-2 production. However, after log transformation to achieve a normal distribution of the data and applying the Bonnferoni correction for multiple comparisons, analysis of variance revealed that only the combination of IL-2 and TGF-β resulted in significant inhibition (p=0.05).

IL-10 production is increased in SLE (Llorente, L. et al. (1993), *Eur Cytokine Network* 4.421–427) and this cytokine can inhibit production of both IL-2 and TGF-β. In 9 cases we also assessed the effect of anti-IL-10, but only a modest decrease of IgG synthesis was observed in some subjects and this difference was not statistically significant. Similarly, TNFα production is also decreased in a subset of patients with SLE (Jacob, C. O. et al. (1990), *Proc Natl Acad Sci* 87:1233–1237). Although this cytokine also increases the production of active TGF-β (Ohtsuka, K. et al. (198), *J Immunol* 160:2539–2545), the addition of TNFα to the cultures had minimal effects (results not shown).

We also examined SLE PBMC for spontaneous production of anti-NP autoantibodies and found significant titers in 4 cases. In all cases exposure of PBMC to either IL-2 or IL-2 and TGF-β inhibited anti-NP production by at least 50 percent. TGF-β by itself was ineffective (Table 2). In these cases the effects of IL-2 by itself was equivalent to that the combination of IL-2 and TGF-β.

TABLE 2

Effect of treating PBMC with IL-2 and TGF-β on Spontaneous Autoantibody production in SLE

| Cytokine treatment | Anti-nucleoprotein antibody (U/ml) | | | |
| --- | --- | --- | --- | --- |
| | Case A: | Case B: | Case C | Case D |
| Nil | 308 (100)* | 312 (100) | 25 (100) | 73 (100) |
| TGF-β (10 pg/ml) | 282 (92) | 298 (96) | 26 (104) | ND |
| IL-2 & TGF-β | 29 (10) | 14 (4.5) | 12 (48) | 35 (48) |
| IL-2 | 23 (7.5) | 10 (3) | 11 (44) | ND |

*Percent of baseline values

PBMC from SLE patients were exposed to IL-2 (10 u/ml) and TGF-β (10pg/ml) for 72 hours. The cells were washed and cultured for seven additional days. Anti-NP released into the supernatants was measured by an ELISA.

Previously we have reported that IL-2 increases the production of biologically active TGF-β (Ohtsuka, K. et al. (1998), *J Immunol* 160:2539–2545). It was, therefore, possible that al least some of the effects of IL-2 on spontaneous Ig synthesis were mediated by TGF-β. This possibility was investigated by determining whether the effects of IL-2 could be reversed by an anti-TGF-β neutralizing antibody. In the example shown in FIG. 3A, the addition of anti-TGF-β did not affect spontaneous IgG synthesis. Antagonism of TGF-β, however, did abolish the inhibitory effects of IL-2 on IgG synthesis. PBMC from this patient (Case C in Table 2) also spontaneously produced anti-NP antibody. Here also anti-TGF-β abolished the inhibitory effects of IL-2 on anti-NP production (FIG. 3B). In this subject, therefore, the inhibitory effects of IL-2 on spontaneous IgG and autoantibody synthesis were mediated by TGF-β. This effect of anti-TGF-β was documented in 4 of 8 cases studied. Thus, the inhibitory effects of IL-2 could either be TGF-β-dependent or independent. Examples of each effect are shown in Table 3.

TABLE 3

Effect of IL-2 and TGF-β on Spontaneous IgG Synthesis in SLE

| Cytokines Added | Patient A: TGF-β dependent inhibition G (μgm/ml) | Patient B: TGF-β independent inhibition IgG (μgm/ml) |
| --- | --- | --- |
| Medium only | 2.5 (100)* | 2.6 (100) |
| TGF-β (10 pg/ml) | 1.4 (56) | 2.5 (96) |
| IL-2 & TGF-β | 0.4 (16) | 0.5 (19) |
| IL-2 & anti-TGF-β | 11.6 (464) | 0.5 (19) |
| IL-2 & IgG1 | 3.6 (144) | 0.6 (23) |

*Percent of baseline IgG synthesis

We had the opportunity to repeat the study of on SLE patient 28 days after initiation of steroid therapy (Table 4). Before treatment spontaneous IgG synthesis was greater than 2 μg/ml of IgG. Exposure of PBMC to IL-2 markedly inhibited IgG production and TGF-β had a moderate effect. Following corticosteroid therapy, spontaneous IgG production decreased by 75%. As before, exposure of PBMC to IL-2 ± TGF-β decreased IgG production by 50%. However, this inhibition was reversed by anti-TGF-β. Here again, this effect of IL-2 could be explained by upregulation of endogenous active TGF-β.

TABLE 4

Effect of Corticosteroid Therapy on Spontaneous IgG Synthesis in SLE

| Cytokines Added | Before Treatment Day 0 | After Treatment Day 28 |
| --- | --- | --- |
| Nil | 2.2 | 0.6 |
| TGF-β (10 pg/ml) | 1.2 | 0.4 |
| IL-2 (10 U/ml) | 0.4 | 0.3 |
| IL-2 & TGF-β | 0.7 | 0.3 |
| IL-2 & anti-TGF-β | ND | 0.8 |
| IL-2 & IgG1 | ND | 0.6 |

*Percent of baseline IgG synthesis

In view of our previous studies in healthy subjects that IL-2 and TGF-β can induce activated CD+ T cells to down-regulate Ig production, we attempted to isolate and treat CD8+ T cells from SLE patients in this study. These experiments were unsuccessful because of the marked variability of spontaneous Ig synthesis and the large amount of blood required from patients with active SLE for cell separation procedures. However, we were able to obtain enough blood from one patient with active SLE to investigate the effect of IL-2 and TGF-β on CD8+ T cell modulation of anti-CD2 induced IgG synthesis. We have recently reported that unlike anti-CD3, a mitogenic combination of anti-CD2 monoclonal antibodies did not induce PBL to produce IgG (Gray, J. D. et al. (1998), *J Immunol* 160:2248–2254). This was because anti-CD2 stimulated NK cells to produce TGF-β, which in turn induced CD8+ T cells to down-regulate Ig production (Gray, J. D. et al. (1998), *J Immunol* 160:2248–2254). In this patient, as we have reported previously (Gray, J. D. et al. (1994), *J Exp Med* 180:1937–1942), CD8+ T cells enhanced IgG synthesis and this enhancement was markedly potentiated by the combination of NK cells and CD8+ T cells (FIG. 4A). By contrast IL-2 and TGF-β abolished the helper effects of SLE CD8+ T cells and enabled these cells to suppress IgG production. This inhibitory effect of IL-2 and TGF-β was dependent upon the presence of CD8+ T cells. (FIG. 4B). Thus, evidence has been obtained that the effects of IL-2 and TGF-β can be mediated by CD8+ T cells.

These studies demonstrate that a short exposure of PBMC to IL-2 and TGF-β can greatly decrease subsequent spontaneous polyclonal IgG and autoantibody production in SLE, especially in patients with severe disease and marked B cell hyperactivity. This study confirms previous reports indicating that IL-2 can inhibit antibody production (Hirohata, S. et al. (1989), *J Immunol* 142: 3104–3112 and Fast, L. D. (1992), *J Immunol* 149:1510–1515) and reveals that picomolar concentrations of TGF-β can contribute to this down-regulation. In the group of 12 patients studied, the inhibitory effect of IL-2 and TGF-β on polyclonal IgG synthesis was greater than the effect of IL-2 alone. However, the inhibitory effects of IL-2 were heterogeneous. In 4 of 8 cases studied, the inhibition was TGF-β-dependent in that a neutralizing anti-TGF-β mAb abolished the effect. In the remaining cases the down-regulatory effects of IL-2 were TGF-β-independent. Similarly, both TGF-β-dependent and independent inhibition of spontaneous anti-NP autoantibody production was documented. We also investigated the effects of antagonizing the IL-10 and adding TNF-α because of previously described abnormalities in the production of these cytokines in SLE (Llorente L. et al. (1993), *Eur Cytokine Network* 4:421–427; Jacob, C. O. et al. (1990), *Proc Natl Acad Sci* 87:1233–1237).

These procedures, however, had minimal effects on spontaneous Ig synthesis where lymphocytes had been activated previously.

Others have reported that the degree of B cell hyperactivity in SLE correlates with disease activity (Blaese, R. M. et al. (1980), *Am J Med* 69:345–350; Klinman, D. M. et al. (1991), *Arthritis Rheum* 34:1404–1410). This was not the case in the present study, possibly because of concurrent drug therapy. In general, those patients with marked spontaneous Ig synthesis were untreated whereas those with less B cell activity were currently receiving prednisone. We presented one case where spontaneous IgG synthesis decreased markedly after corticosteroid therapy was begun. This patient's B cells had also been secreting anti-NP antibody before treatment, and production of this autoantibody became undetectable after steroid therapy (result not shown).

TGF-β consists of a multifunctional family of cytokines important in tissue repair, inflammation and immunoregulation (Massague, J. (1990), *Annu Rev Cell Biol* 6597–641). TGF-β is different from most other cytokines in that it is secreted as an inert precursor molecule and converted to its biologically active form extracellularly (Massague, J. (1990), *Annu Rev Cell Biol* 6597–641; Flaumenhaft, R. et al. (1993), *Adv Pharmacol* 24:51–76). Regulatory T cells in various experimental autoimmune models such as experimental autoimmune encephalitis (Weiner, H. L. et al. (1994), *Annu Rev Immunol* 12:809–837) and colitis (Neurath, M. F. et al. (1996), *J Exp Med* 183:2605–2516) produce this cytokine. TGF-β is immunosuppressive in nanomolar concentrations and can inhibit T and B cell proliferation, NK cell cytotoxic activity and the generation of T cell cytotoxicity (Letterio, J. J. et al. (1998), *Ann Rev Immunol* 16:137–162). By contrast, TGF-β has been reported to promote the growth of murine CD4+ cells and CD8+ cells (Kehrl, J. H. et al. (1986), *J Exp Med* 163:1037–1050; Lee, H. M. et al. (1993), *J Immunol* 151:668–677) and can promote B cell differentiation (Van Vlasselaer, P. et al. (1992), *J Immunol* 148:2062–2067).

In our previous studies with lymphocytes from healthy subjects to generate regulatory T cells, the picomolar concentrations of TGF-β used were smaller than that required for inhibition of T or B cell function (Gray, J. D. et al. (1998), *J Immunol* 160:2248–2254; Gray, J. D. et al. (1994), *J Exp Med* 180:1937–1942). Similar concentrations were used in the present studies with SLE patients and TGF-β by itself had modest inhibitory effects on Ig synthesis. As before, a combination of IL-2 of TGF-β produced the most potent inhibition. In our previous studies, this effect was mediated by CD8+ T cells.

IL-2 has well established effects on the induction of T suppressor cell activity (Hirohata, S. et al. (1989), *J Immunol* 142:3104–3112; Fast, L. D. *J Immunol* 149:1510–1515), but whether these effects are direct or indirect is unclear. In mice deletion of the IL-2 gene results in massive lymphoproliferation and autoimmune disease (Sadlack, B. et al. (1995), *Eur J Immunol* 25:3053–3059). In SLE, a negative correlation was reported between IL-2 levels and B cell hyperactivity (Huang, Y. P. et al. (1988), *J Immunol* 141:827–833). Previously, we attempted to inhibit spontaneous Ig production in SLE with IL-2, but the results, however were extremely variable. While we observed strong inhibition in some cases, in others IL-2 markedly increased Ig production. We believe that the timing and the cytokine millieu explains the more consistent inhibition observed in this study. Here the IL-2 and TGF-β were present only during the initial 72 hours of culture rather than the entire culture period. Enhancement of Ig synthesis in the latter case could be explained by the positive effects of IL-2 on B cell differentiation (Coffman, R. L. et al. (1988), *Immunol Rev* 102:5–28). IL-2 can down-regulate antibody production by several mechanisms. In addition to the TGF-β circuit described in the report, IL-2 induced inhibition can occur by up-regulation of IFN-γ (Noble, A. et al. (1998), *J Immunol* 160:566–571), or by cytolytic mechanisms (Stohl, W. et al. (1998), *J Immunol* 160:5231–5238; Esser, M. T. et al. (1997), *J Immunol* 158:5612–5618). Previously, we had investigated the regulatory effects of NK cells on antibody synthesis and reported that while the direct effect of NK cells is to up-regulate IgG synthesis (Kinter, A. et al. (1995), *Proc Natl Acad Sci USA* 92:10985–10989), these lymphocytes have the opposite effect when cultured with CD8+ T cells in healthy subjects (Gray, J. D. et al. (1994), *J Exp Med* 180:1937–1942). In SLE patients, however, the combination of CD8+ T cells and NK cells enhanced IgG production (Linker-Israeli, M. et al. (1990), *Arthritis Rheum* 33:1216–1225). This was again observed in the present report. While in the normal subject the addition of NK cells to CD8+ T cells markedly inhibited anti-CD2 stimulated IgG synthesis, the opposite was observed in SLE. From studies of normals we had learned that NK cell-derived TGF-β induced co-stimulated CD8+ T cells to down-regulate IgG and IgM production (Gray, J. D. et al. (1998), *J Immunol* 160:2248–2254). In this study IL-2 and TGF-β induced moderate suppressive activity by CD8+ T cells. It is likely, therefore, that in SLE at least one way that IL-2 and TGF-β inhibit B cell activity is by generating regulatory T cells. In addition, other lymphocyte populations treated with these or other cytokines may also down-regulate B cells activity in SLE.

Example 2

The Correlation of TGF-β Production to Disease Activity and Severity

Having shown that the lymphocyte production of the total and active forms of TGF-β is decreased, we next asked whether these defects correlate with disease activity and/or severity. TGF-β1 production by blood lymphocytes from 17 prospectively studied SLE patients was compared with 10 rheumatoid arthritis (RA) patients and 23 matched healthy controls. In RA the levels of active TGF-β1 were lower than controls, but not deceased to the extent found in SLE. Levels of constitutive and anti-CD2 stimulated active TGF-β1 detected in picomolar amounts were markedly reduced in 6 untreated patients hospitalized with recent onset, very active and severe SLE and similarly reduced in 11 patients with treated, less active disease. thus, decreased production of active TGF-β1 did not correlate with disease activity. By contrast, decreased production of total TGF-β1 inversely correlated with disease activity. Thus it appears that although impaired lymphocyte secretion of the latent precursor of TGF-β1 may result as a consequence of disease activity, the ability to convert the precursor molecule to its active form may be an intrinsic cellular defect. Insufficient exposure of T cells to picomolar concentrations amounts of TGF-β1 at the time they are activated can result in impaired down-regulation of Ig synthesis. Thus, decreased lymphocyte production of active TGF-β1 in SLE can contribute to B cell hyperactivity characteristic of this disease.

Methods

Study Subjects

Seventeen subjects with a diagnosis of SLE who fulfilled the American College of Rheumatology criteria for the classification of SLE (Tan, E. M. et al. (1982), *Arthritis Rheum* 25:1271–1277), 10 subjects with RA who fulfilled the ACR 1987 revised criteria for the classification of RA (Arnett, F. C. et al. (1988), *Arthritis Rheum* 31:315–324), and 23 healthy donors were studied. The SLE group consisted of 15 women and 2 men (15 Hispanic, 1 African American, 1 Asian). The mean age was 34.5 years (range, 20–75 years). Six patients were hospitalized, and 11 were attending an outpatient clinic. All of the hospitalized patients were untreated before admission and were studied before they received their first dose of corticosteroids. Outpatients were receiving less than 20 mg of prednisone, and none were receiving cytotoxic drugs. Disease activity was assessed with the SLAM (Liang, M. H. et al. (1989), *Arthritis Rheum* 32:1107–1118) and SLEDAI (Bombardier, C. et al. 1992), *Arthritis Rheum* 35:630–640) indices with mean values of 6.6 and 7.6, respectively. The RA group consisted of 9 women and 1 man (9 Hispanic, 1 Asian). The mean age was 50.9 years (range, 39–67 years). All of the patients were attending the outpatient clinic and had mild to moderately active disease. The mean duration of disease was 9.5 years. One patient received myochrysine, 3 patients received prednisone (1, 1 and 20mg), 3 patients received methotrexate, and one patient received sulphasalazine. Healthy donors served as controls and were matched as closely as possible for age, sex, and ethnic groups.

TABLE 5

Clinical Characteristics of Two Groups of SLE Patients

| Clinical Data | Hospitalized (n = 6) | Outpatient (n = 11) | p Value |
| --- | --- | --- | --- |
| Age | 26.8 | 38.6 | 1.037 |
| Sex (F/M) | 6/0 | 9/2 | |
| Ethnic Group (H/AA/A) | 5/0/1 | 10/1/10 | |
| Disease Duration (yr) | 0.71 | 8.25 | 0.051 |
| Disease Activity | | | |
| SLAM | 13.3 | 2.9 | 0.014 |
| SLEDAI | 15.7 | 4.1 | 0.006 |
| Prednisone dose (mg/day) | 41.2 | 7.8 | 0.008 |
| Active Renal disease | 83% | 9% | 0.028 |
| Hemolytic Anemia | 67% | 9% | 0.064 |
| Anti-DNA (titer) | 466.7 | 33.0 | 0.064 |
| C3 | 47.5 | 98.6 | 0.008 |
| C4 | 13.7 | 18.6 | 0.127 |

Reagents

Antibodies used were supernatants of hybridomas secreting anti-CD2 (OKT11, American Type Culture Collection (ATCC), Rockville, Md., and GT2 made available by Dr. Alain Bernard, Nice, France). A monoclonal antibody recognizing TGF-β isoforms 1, 2 & 3 (1D 11), an antibody against TGF-β isoforms 2 & 3 (3C7), and rTGF-β2 were kindly provided by Dr. Bruce Pratt (Genzyme Pharmaceuticals, Farmington, Mass.).

Isolation of Blood lymphocytes

Peripheral blood mononuclear cells (PBMC) were prepared from heparinized venous blood by Ficoll-Hypaque (Pharmacia, Piscataway, N.J.) density gradient centrifugation using methods described previously (Ohtsuka, K. et al. (1998), *J Immunol* 160:2539–2545). The mononuclear cells were washed in PBS with 5 mM EDTA (Life Technologies, Grand Island, N.Y.) to remove platelets, which are a rich source of TGF-β. Peripheral blood lymphocytes (PBL) were separated from PBMC by centrifugation through a continuous Percoll (Pharmacia) density gradient. The percentage of monocytes remaining in the high density, lymphocyte-enriched fraction was somewhat higher in SLE (8.5% vs 4.3%).

Cell Culture Procedures

Procedures for cell cultures have been described previously ((Ohtsuka, K. et al. (1998), *J Immunol* 160:2539–2545). In brief, $1 \times 10^5$ of the lymphocytes were added to the wells of 96-well flat bottom microtiter plate (Greiner Rocky Mountain Scientific, Salt Lake City Utah). The cultures were carried out in AIM-V serum free medium (Life Technologies), since serum contains significant amount of latent TGF-β. Anti-CD2 was used at the optimal concentrations to induce TGF-β production (GT2 1:40 and T11 1:80) hybridoma culture supernatants. Previous studies have revealed that anti-CD2 strongly stimulates PBL to produce TGF-β (Gray, J. D. et al. (1998), *J Immunol* 160:2248–2254).

TGF-β Assay

Mink lung epithelial cells (MLEC) which had been transfected with an expression construct containing a plasminogen activator inhibitor (PAI-1) promoter fused to luciferase reporter gene were kindly provided by Dr D. B. Rifkin, New York, N.Y. MLEC at $2 \times 10^4$/well were incubated with 200μl supernatants for 18 h at 37° C. To assay for luciferase activity, MLEC were lysed by a cell lysis reagent (Analytical Luminescence, Ann Arbor, Mich.). Cell lysates were then reacted with assay buffer and luciferin solution (both from Analytical Luminescence) immediately before being measured in a luminometer (Lumat, Berthold Analytical Instruments Inc., Nashua, N.H.). To measure total TGF-β activity, samples were heated at 80° C. for 3 minutes to release the active cytokine from the latent complex. Active TGF-β activity was measured without heating of supernatants. In all assays, several concentrations of rTGF-β were included to generate a standard curve. The variability of replicate cultures was less than 10 percent (Ohtsuka, K. et al. (1998), *J Immunol* 160:2539–2545).

Statistical Analysis

The significance of the results was analyzed using the Mann-Whitney test and Spearman rank correlation performed using GBSTAT software (Professional Statistics and Graphics Computer Program, Dynamic Microsystems Inc., Silver Spring, Md.).

We measured constitutive and stimulated TGF-β1 produced by PBL from patients with SLE or RA, and compared these values with those from normal controls. The cytokine detected in culture supernatants was neutralized by a mAb recognizing isoforms 1, 2, & 3, but not by one against isoforms 2 & 3, a result confirming the production of TGF-β1. Compared to normal controls, constitutive production of active TGF-β1 was significantly decreased in SLE (14±5 vs 56±21 pg/ml, p=0.02, FIG. 5). Anti-CD2 stimulated active TGF-β1 was also decreased (87±22 vs 399±103 pg/ml, p=0.003). In RA, the mean value for constitutive TGF-β1 was similar to that of SLE (19±5 pg/ml) and after stimulation by anti-CD2 was intermediate between normal and SLE (197±54 pg/ml).

Constitutive total TGF-β1 produced by lymphocytes was also decreased in SLE in comparison with the normal group (286±82 vs 631±185 pg/ml, p=0.05). The value in RA was intermediate between normal and SLE (435±161 pg/ml). Following the addition of anti-CD2, total TGF-β1 increased in SLE somewhat more than in normal controls so that the differences were not statistically significant. Values in the RA group were again intermediate between the normal and SLE group.

To look for a possible relationship between decreased levels of TGF-β1 and disease activity, we compared hospitalized SLE patients with those seen in the outpatient clinic. The clinical characteristics of these two groups are summarized in Table 5. Those that were hospitalized were younger; 5 of 6 had symptoms for less than 3 months; they had markedly active disease; and most had severe SLE with nephritis and/or hemolytic anemia. The outpatient group by contrast, had chronic disease which had become less active following treatment. Notwithstanding this marked difference in disease heterogeneity, duration, activity, and severity, both constitutive and stimulated active TGF-β1 production were significantly decreased in both groups in comparison with normal controls (Table 6).

TABLE 6

Comparison of TGF-β1 Production by Lymphocytes from Two Groups of Patients with SLE*

|  | Normal (n = 23) | SLE Group 1 (n = 6) | SLE Group 2 (n = 11) |
| --- | --- | --- | --- |
| Active TGF-β1 (pg/ml) | | | |
| Constitutive | 56 ± 21 | 21 ± 14† | 10 ± 4† |
| CD2 stimulated | 399 ± 103 | 117 ± 52† | 70 ± 19‡ |
| Total TGF-β1 (pg/ml) | | | |
| Constitutive | 631 ± 185 | 132 ± 44† | 365 ± 120 |
| CD2 stimulated | 771 ± 136 | 226 ± 74† | 667 ± 166 |

*PBL 1 × $10^5$/well were cultured for 48 h, and the supernatants were tested for TGF-β1.

When we looked for correlations between levels of active and total TGF-β1 with disease activity, there was a significant negative correlation between anti-CD2 stimulated production of total TGF-β1 and the SLEDAI (r=−0.55, p=0.03, but not the SLAM index (−0.43, p=11). The SLEDAI index is weighted for central nervous system involvement and renal disease. Thus, an impaired capacity for lymphocytes to secrete the precursor form of TGF-β1 appears to be associated with severe disease. The Levels of active TGF-β1 did not correlate with disease activity.

The principal finding in this example is that decreased production of active TGF-β1 in SLE does not correlate with disease activity or severity. Decreased amounts of constitutive and stimulated active TGF-β1 were found in both patients with recent onset and established disease. Moreover, the values did not correlate with activity, as measured by the SLAM and SLEDAI indices, or severity as assessed by vital organ involvement. However, while total TGF-β1 production was also decreased in SLE, this defect appeared to correlate with disease activity. It was found chiefly in hospitalized SLE patients. The finding that total TGF-β1 production correlated most strongly with the SLE-DAI index, which is weighted for major organ system involvement, also suggests a relationship with disease severity.

This study also included a control group of RA patients whose disease activity was comparable to SLE patients with established disease. Although TGF-β1 values in the RA group was somewhat less than the normal controls, with the exception of constitutive active TGF-β1, the magnitude of the defect was not as marked as in SLE and was not statistically significant Previously, we have documented that NK cells are the principal lymphocyte source of TGF-β and the only lymphocyte population to constitutively produce this cytokine in its active form (Gray, J. D. et al. (1998), *J Immunol* 160:2248–2254). It was of interest, therefore, to find that constitutive production of NK cell-derived TGF-β was decreased in SLE. We also learned that both IL-2 and TNF-α could enhance the production of active TGF-β. Production of both of these cytokines are decreased in SLE (Gray, J. D. et al. (1994), *J Exp Med* 180:1937–1942). However, in most patients exogenous IL-2 and TNF-α could not restore TGF-β production to normal (Example 2). IL-10 production is increased in SLE (Llorente, L. et al. (1993), *Eur Cytokine Network* 4:421) and correlations between elevated levels and disease activity have been reported (Housslau, F. A. et al. (1995), *Lupus* 4:393–395; Haglwara, E. et al. (1996), *Arthritis Rheum* 39:379). IL-10 can inhibit IL-2, TNF-α and TGF-β production (Example 2 and Moore, K. W. et al. (1993), *Ann Rev Immunol* 11:165–190). The findings that production of active TGF-β is decreased in patients with mild as well as active disease, and that we could only partially reverse the production defect by antagonizing IL-10 (Example 2), suggests that increased IL-10 production, by itself, cannot account for decreased lymphocyte production of active TGF-β1 in SLE. Several mechanisms are probably involved. It is likely that one or more defects in the extracellular conversion of the latent precursor to the mature, active form may explain this abnormality.

Although TGF-β has well documented inhibitory properties on lymphocyte proliferation and effector cell function (Letterio, J. J. et al. (1998), *Ann Rev Immunol* 16:137–162), stimulatory properties have also been reported (Lee, H. M. et al. (1991), *J Immunol* 151:668–677). TGF-β modulates cytokine production by stimulated T cells as well as upregulating its production. In mice, TGF-β1 selectively activates CD8+ T cells to proliferate (Lee, H. M. et al. (1991), *J Immunol* 151:668–677), and augments the maturation of naive cells to memory T cells (Lee, H. M. et al. (1991), *J Immunol* 147:1127–1133). in humans TGF-β1 is a potent inducer of effector T cells (Cerwenka, A. et al. (1994), *J Immunol* 153:4367–4377). While large (nanogram/ml) quantities are required for immuno-suppressive effects, we have shown that only small (picogram/ml) quantities are needed to co-stimulate CD8+ T cells for down-regulatory effects on antibody production (Gray, J. D. et al. (1998), *J Immunol* 160:2248–2254).

These studies suggest, therefore, that while impaired lymphocyte secretion of the latent precursor of TGF-β1 may result as a consequence of disease activity, decreased active TGF-β1 production in SLE is more complex and may result from several different mechanisms. We have proposed that programming naive T cells to down-regulate antibody production requires the presence of pg/ml quantities of active TGF-β at the time they are activated and have evidence to support this suggestion (Gray, J. D. et al. (1998), *J Immunol* 160:2248–2254). Therefore, a lack of picomolar amounts of active TGF-β in the local environment at a critical time could possibly account for ineffective T cell regulatory function to control B lymphocyte activity in SLE.

Example 3

Treating SLE with Mitogens

In this example, IgG production is down regulated by treating the cells with an inhibitory composition comprising a mitogen such as Con A. The cells are prepared as outlined in the above examples, and then they are incubated with mitogens to augment the population of cells that down regulate antibody production. In this case, the cells are incubated with physiological concentrations of Con A for 4 to 72 hours using standard incubation techniques. The concentration of Con A used can range from about 0.01 to about 10 micrograms/ml with 1 microgram/ml being presently preferred. Con A is available from Sigma (St. Louis, Mo.).

Although it is not known how the mitogens work, it is believed to induce the production of TGFβ by monocytes in the PBMCs preparation, and the TGFβ then acts on T cells to become antibody suppressor cells.

The cells are then washed, if necessary, and transplanted back into the patient.

Example 4

Treating Cells with a Mixture of Cytokines and Mitogens

In this example, IgG production is down regulated by treating the cells with an inhibitory composition comprising a mixture of cytokine and mitogen. The cells are prepared as outlined in the above examples, and then they are incubated with the mixture to augment the population of cells that down regulate antibody production, such as physiological concentrations of Con A, IL-2 and TGFβ, or Con A and IL-2, for 4 to 72 hours using standard incubation techniques.

After the cells have been incubated with the cytokines and mitogen, the cells are then washed with HBBS to remove any cytokine and mitogen that are in the solution. The cells are then suspended in 200–500 ml of HBBS and are reintroduced into the mammal.

What is claimed is:

1. A method for treating an autoimmune disorder in a patient comprising:
   a) removing peripheral blood mononuclear cells (PBMC) from said patient;
   b) treating said cells with an inhibitory composition for a time sufficient to suppress immunoglobulin production; and
   c) reintroducing said cells to said patient.

2. A method according to claim 1 wherein said inhibitory composition comprises IL-2.

3. A method according to claim 1 wherein said inhibitory composition comprises a mixture of IL-2 and TGF-β.

4. A method according to claim 1 wherein said inhibitory composition comprises a CD2 activator.

5. A method according to claim 1 wherein said autoimmune disorder is systemic lupus erythematosus (SLE).

* * * * *